US008748159B2

(12) United States Patent
Fleming et al.

(10) Patent No.: US 8,748,159 B2
(45) Date of Patent: *Jun. 10, 2014

(54) METHOD AND APPARATUS FOR VIABLE AND NONVIABLE PROKARYOTIC AND EUKARYOTIC CELL QUANTITATION

(75) Inventors: James E. Fleming, Spokane, WA (US); Jason Buck Somes, Spokane, WA (US); Darby McLean, Spokane, WA (US); Jerad R. Holcomb, Spokane, WA (US)

(73) Assignee: GenPrime, Inc., Spokane, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/284,693

(22) Filed: Oct. 28, 2011

(65) Prior Publication Data

US 2012/0164677 A1 Jun. 28, 2012

Related U.S. Application Data

(60) Continuation of application No. 13/026,135, filed on Feb. 11, 2011, now Pat. No. 8,071,326, which is a continuation of application No. 12/340,044, filed on Dec. 19, 2008, now Pat. No. 7,906,295, which is a division of application No. 11/144,244, filed on Jun. 2, 2005, now Pat. No. 7,527,924, which is a division of application No. 09/912,266, filed on Jul. 24, 2001, now abandoned.

(60) Provisional application No. 60/220,298, filed on Jul. 24, 2000.

(51) Int. Cl.
*C12N 1/00* (2006.01)
*G01N 33/53* (2006.01)

(52) U.S. Cl.
USPC .......... 435/254.21; 435/4; 435/7.2; 435/7.31; 435/7.72; 435/18; 435/19; 435/29; 435/39; 435/173.9; 435/374; 436/63; 436/164; 436/172; 436/10; 422/73; 422/82.08

(58) Field of Classification Search
USPC ................ 435/2, 4, 7.2, 7.31–7.37, 7.72, 7.8, 435/7.92, 18, 19, 173.9, 286.1, 374, 29, 39, 435/254.21; 436/63, 164, 172, 10; 422/73, 422/82.08
See application file for complete search history.

(56) References Cited

U.S. PATENT DOCUMENTS 3,586,859 A 6/1971 Katz et al.
4,783,401 A 11/1988 Horan et al.
(Continued)

FOREIGN PATENT DOCUMENTS

WO 9202632 A1 2/1992

OTHER PUBLICATIONS

Breeuwer et al. Energy Dependent, Carrier-Mediated Extrusion of Carboxyfluorescein from *Saccharomyces cereviseae* Allows Rapid Assessment of Cell Viability by Flow Cytometry, Applied and Environmental Microbiology 60(5): 1467-1472 (May 1994).*

(Continued)

*Primary Examiner* — Gail R Gabel
(74) *Attorney, Agent, or Firm* — Cooley LLP

(57) ABSTRACT

A rapid method for the quantitation of various live cell types is described. This new cell fluorescence method correlates with other methods of enumerating cells such as the standard plate count, the methylene blue method and the slide viability technique. The method is particularly useful in several applications such as: a) quantitating bacteria in milk, yogurt, cheese, meat and other foods, b) quantitating yeast cells in brewing, fermentation and bread making, c) quantitating mammalian cells in research, food and clinical settings. The method is especially useful when both total and viable cell counts are required such as in the brewing industry. The method can also be employed to determine the metabolic activity of cells in a sample. The apparatus, device, and/or system used for cell quantitation is also disclosed.

19 Claims, 10 Drawing Sheets

(56) References Cited

U.S. PATENT DOCUMENTS

| | | | |
|---|---|---|---|
| 5,436,134 | A | 7/1995 | Haugland et al. |
| 5,437,980 | A | 8/1995 | Haugland |
| 5,563,070 | A | 10/1996 | Yamamoto et al. |
| 5,582,984 | A | 12/1996 | Bieniarz et al. |
| 5,658,751 | A | 8/1997 | Yue et al. |
| 5,939,282 | A | 8/1999 | Harman et al. |
| 6,277,655 | B1 | 8/2001 | Sarkadi et al. |
| 6,673,568 | B1 | 1/2004 | Fleming et al. |
| 7,527,924 | B2 | 5/2009 | Fleming et al. |
| 7,906,295 | B2 | 3/2011 | Fleming et al. |
| 8,071,326 | B2 * | 12/2011 | Fleming et al. ............ 435/7.31 |
| 2002/0119438 | A1 | 8/2002 | Kato |

OTHER PUBLICATIONS

Breeuwer et al. Characterization of Uptake and Hydrolysis of Fluorescein Diacetate and Carboxyfluorescein Diacetate by Intracellular Esterases in *Saccharomyces cerevisiae,* Which Result in Accumulation of Fluorescent Product, Applied and Environmental Microbiology 1614-1619 (Apr. 1995).*

Allen, "The Microbrewery Laboratory Manual—A Practical Guide to Laboratory Techniques and Quality Control Procedures for Small-Scale Brewers," Brewing Techniques 2(4):28-35, 1994.

Breeuwer et al., "Energy-dependent, carrier-mediated extrusion of carboxyfluorescein from *Saccharomyces cerevisiae* allows rapid assessment of cell viability by flow cytometry," Appl. Environ. Microbiol. 60(5):1467-1472, 1994.

Breeuwer et al., "Characterization of uptake and hydrolysis of fluorescein diacetate and carboxyfluorescein diacetate by intracellular esterases in *Saccharomyces cerevisiae,* which result in accumulation of fluorescent product," Appl. and Environ. Microbiol. 61(4):1614-1619, 1995.

Carvell et al., "Developments in using off-line radio frequency impedance methods for measuring the viable cell concentration in the brewery," Journal of the American Society of Brewing Chemists 58(2):57-62, 2000.

Catt et al., "Hoechst staining and exposure to UV laser during flow cytometric sorting does not affect the frequency of detected endogenous DNA nicks in abnormal and normal human spermatozoa," Mol. Hum. Reprod. 3(9):821-825, 1997.

Ferguson and Denny, "Microbial mutagenic effects of the DNA minor groove binder pibenzimol (Hoechst 33258) and a series of mustard analogues," Mutat. Res. 329(1):19-27, 1995.

Griffith et al., "An evaluation of luminometry as a technique in food microbiology and a comparison of six commercially available luminometers," Food Science and Technology Today 8(4):209-216, 1994.

Guldfeldt et al., "Relationship Between Yeast Cell Proliferation and Intracellular Esterase Activity During Brewing Fermentations," J. Inst. Brew. 104:333-338, 1998.

Kawai et al., "Rapid enumeration of physiologically active bacteria in purified water used in the pharmaceutical manufacturing process," J. Appl. Microbiol. 86(3):496-504, 1999.

Koch et al., "Fluorescence microscopy procedure for quantitation of yeasts in beverages," Appl. and Environ. Microbiol. 52(3):599-601, 1986.

Kovařík et al., "Estimation of viable cell count after fluorescein diacetate standing using phosphoimager analysis," Biotechniques 27(4):685-688, 1999.

Latt and Wohlleb, "Optical studies of the interaction of 33258 Hoechst with DNA, chromatin, and Metaphase Chromosomes," Chromosoma 52(4):297-316, 1975.

Mochaba et al., "Practical procedures to measure yeast viability and vitality prior to pitching," Journal of the American Society of Brewing Chemists 56(1):1-6, 1998.

O'Connor-Cox et al., "Methylene blue staining: use at your own risk," Tech. Q. Master Brew. Assoc. Am. 34(1):306-312, 1997.

Prosperi, "Intracellular turnover of Fluorescein diacetate. Influence of membrane ionic gradients on Fluorescein efflux," Histochem. J. 22(4):227-233, 1990.

Smart et al., "Use of Methylene Violet Staining Procedures to Determine Yeast Viability and Vitality," Journal of the American Society of Brewing Chemists 57(1):18-23, 1992.

Steward et al., "A new methodology for plant cell viability assessment using intracellular esterase activity," Plant Cell Reports 19(2):171-176, 1999.

* cited by examiner

An example of solid calibration standards for ultraviolet and visible wavelengths that can be used with the Turner Designs Hand-Held picofluor fluorometer.

| Easy Count Reading | (cells/ml = Easy Count Reading X 154578 - 17131723) |
|---|---|
| 7000 | $1.1 \times 10^9$ |
| 6000 | $9.1 \times 10^8$ |
| 5000 | $7.6 \times 10^8$ |
| 4500 | $6.8 \times 10^8$ |
| 4000 | $6.0 \times 10^8$ |
| 3500 | $5.2 \times 10^8$ |
| 3000 | $4.5 \times 10^8$ |
| 2000 | $2.9 \times 10^8$ |
| 1000 | $1.4 \times 10^8$ |

FIG. 2

(Cells/ml= Easy Count Reading X 163343 - 26930879)

| Easy Count Reading | |
|---|---|
| 7000 | $1.1 \times 10^9$ |
| 6000 | $9.5 \times 10^8$ |
| 5000 | $7.9 \times 10^8$ |
| 4500 | $7.1 \times 10^8$ |
| 4000 | $6.3 \times 10^8$ |
| 3500 | $5.4 \times 10^8$ |
| 3000 | $4.6 \times 10^8$ |
| 2000 | $3.0 \times 10^8$ |
| 1000 | $1.4 \times 10^8$ |

FIG. 3

Regression plot showing the relationship between Easy Count fluorescent readings and total cell concentrations of yeast as determined by the methylene blue method.

No. Live Cells = -26930878.718 + 163342.859 * EC Fluorescence Live; R^2 = .977

Regression plot showing the relationship between Easy Count readings and viable cell concentrations of yeast as determined by the methylene blue method.

EasyCount = 958.81 + 25.098 * Hemacytometer corrected for viability(M/cells/ml); R^2 = .987

METHOD AND APPARATUS FOR VIABLE AND NONVIABLE PROKARYOTIC AND EUKARYOTIC CELL QUANTITATION

CROSS REFERENCE TO RELATED APPLICATION

This application is a continuation application of U.S. patent application Ser. No. 13/026,135, filed Feb.11, 2011, now U.S. Pat. No. 8,071,326; which is a continuation application of U.S.patent application Ser. No. 12/340,044, filed Dec. 19, 2008, now U.S. Pat. No. 7,906,295; which is a divisional application of U.S. patent application Ser. No. 11/144,244, filed Jun. 2, 2005, now U.S. Pat. No. 7,527,924, issued May 5, 2009; which is a divisional application of U.S. patent application Ser. No. 09/912,266, filed Jul. 24, 2001, now abandoned; which claims priority to U.S. Provisional Application No. 60/220,298, filed Jul. 24, 2000.

BACKGROUND OF THE INVENTION

1. Technical Field

The present invention relates to methods for the rapid quantitation of both viable and nonviable cells. More specifically, the invention involves incubating cells with a metabolically activated visible fluorescent dye and measuring the fluorescence generated by viable cells. Total cell populations (viable+nonviable) are separately determined by measuring the native UV fluorescence of the cells. The two fluorescence readings are directly related to the number of viable and nonviable cells. This permits the user to determine the percent viability of a mixed population of live and dead cells.

2. Description of the Related Art

The ability to quantify living cells is vitally important to the food, beverage, pharmaceutical, environmental, manufacturing and clinical industries. Several methods are currently employed by these industries to quantify prokaryotic and eukaryotic cells. These methods include, but are not limited to, the standard plate count, dye reduction and exclusion methods, electrometric techniques, microscopy, flow cytometry, bioluminescence and turbidity.

The standard plate count permits the quantitation of living cells (or clumps of cells) also known as colony forming units (cfu) when the cells are grown on the appropriate medium under optimal growth conditions (*Microbial Ecology*, Atlas, R. M. and Bartha, R., Addison Wesley, Longman, N.Y., 1998). Current standards of viable organism counts are often based on the standard plate count, particularly in the food industry. However, colony counts are difficult to interpret since bacteria often clump or form chains that can give rise to significantly inaccurate estimations of the total number of viable organisms in a sample. Also, bacteria, for example, can be in a "metabolically damaged" state and not form countable colonies on a given medium. This problem is more severe when selective media are used. Thus, the standard plate count does not provide a definitive count of viable cells in a sample, which may be very important for certain purposes. Given these factors, such testing also requires skilled technicians who can distinguish individual colony forming units and who can aid in selecting appropriate growth medium. Moreover, the technique is not useful when rapid determination of cell counts is required, since it often requires over 24 hours to obtain results.

Other tests, such as dye reduction tests, rely on the ability of cells to oxidize or reduce a particular dye (Harrington, 1998). Such methods are used to measure the activity of metabolically active organisms rather than provide a measure of the total number of viable cells in a sample. Dyes, such as methylene blue, coupled with microscopic counting, are routinely employed to determine the relative number of microorganisms. The technique is widely employed but nevertheless suffers from factors that must be held constant during the assay, e.g., medium used, chemical conditions, temperature and the types of cells being examined. Also, dye reduction tests that incorporate microscopic counting techniques require trained technical personnel and often depend on subjective interpretations.

Dye exclusion methods of cell quantitation depend on the living cells having the ability to pump the dye out of the cell and into the surrounding fluid medium. While the dye may enter the interior of both living and dead cells, dead cells are not capable of actively pumping the dye out under the conditions normally used. Dye exclusion is commonly employed to enumerate animal, fungal and yeast cells. It is a method requiring skill, correct timing and proper choice of dye. It is not applicable to certain microbes and it yields incorrect viable counts with stressed cells.

An accurate estimation of the number of viable yeast cells in a sample can be obtained by the slide viability technique (Gilliland, 1959). The yeast cells are suspended in a growth medium containing 6% gelatin and the suspension is placed in a hemacytometer slide. The cell suspension is incubated for approximately 20 hours and the numbers of micro colonies are counted. Cells that form micro colonies are viable and dead cells remain as single cells. This technique is considered by the brewing industry to be the most definitive test for counting the number of viable yeast cells. Unfortunately, the long incubation time makes it unacceptable as a routine method.

Microscopic techniques typically involve counting a dilution of cells on a calibrated microscopic grid, such as a hemacytometer. A recent improvement in this technique is the direct epifluorescent filter technique (DEFT) (Pettipher et al, 1989). In this technique, samples are filtered through a membrane filter that traps the cells to be counted. A fluorescent dye is attached to the cells, which are illuminated with ultraviolet light and counted. Unfortunately, the technique requires the use of an expensive microscope and a trained individual or an expensive automated system (Pettipher et al., 1989).

Yet other methods of quantitation use flow cytometry, which involves the differential fluorescent staining of cells suspended in a relatively clear fluid stream of low viscosity. The cell suspension is mixed with the fluorescent dye and illuminated in a flow cell by a laser or other light source. The labeled cells are automatically detected with the use of a fluorescence detector focused on the cells (Brailsford and Gatley, 1993 and Pinder et al., 1993). The technique requires, and is limited by, expensive equipment. Some flow cytometric devices have been used by the food and dairy industry, but their application has been limited by the high cost of instrumentation.

Bioluminescence has been routinely employed in the food sanitation industry to detect and quantify viable organisms and cells. The method involves the use of luciferin-luciferase to detect the presence of ATP (Harrington, 1998 and Griffith et al., 1994). When used to quantify cells, the technique depends on the assumption that there is a constant amount of ATP in a living cell. ATP levels vary in a single cell over more than two orders of magnitude, making this method a relatively inaccurate technique for the enumeration of viable organisms in a sample.

Turbidity of a liquid sample can also be measured as an indication of the concentration of cells due to the light scattering and absorbing qualities of suspended cells (Harrington, 1998). The method is old but it is still employed to estimate the bacterial concentration in a sample. The method is rapid and simple but is highly inaccurate since all cells, particles and substances, including non-living particulate matter, interfere with the interpretation of the results.

The present invention for the quantitation of both viable and nonviable cells is designed to overcome at least five problems that have been identified within the field. First, the new technology circumvents the need for training personnel in how to plate, grow and count viable cells from colonies on agar plates. It also eliminates nearly all training and maintenance costs associated with most of the other methods. Second, the invention substantially decreases the time needed to determine concentrations of cells such as yeast and bacteria. Under current methodologies, quantification requires from 24-72 hours (plate count and enrichment cultures), while the present invention permits accurate quantitation in less than 15 minutes. The methylene blue test is rapid; however, the accuracy is unacceptable for cultures that are less than 90% viable. The slide viability test is accurate for large viability ranges but the time required for results is not suitable for routine use. Third, the new test is accurate over wide ranges of viability and has precision similar to the slide viability test. Fourth, the instant invention offers substantial cost savings over existing methods of cell quantitation. Fifth, the invention permits the simultaneous determination of both viable and total cells in a sample. This allows the user to accurately establish the percent viability of a cell sample (the number of viable cells to total cells). Percent viability is a crucial measurement in many industries such as the dairy and beer brewing industries and is currently carried out by the methylene blue test.

BRIEF SUMMARY

The present invention generally provides methods, kits, and devices for detecting and quantitating the number and/or percentage of viable cells in a sample. In one aspect the invention provides a method for determining the percent viability of cells in a sample, comprising providing a sample containing said cells, detecting the total cell count, contacting said cells with molecule or dye that is detectably altered by enzymatic activity of a viable cell, detecting enzymatically altered dye or molecule, thereby detecting the number of viable cells and comparing the number of total cells with the number of viable cells thereby determining the percent viability.

In another aspect, a method for detecting viable cells is provided that comprises providing a sample containing cells, contacting said sample with a dye that diffuses or is transported into said cells and wherein said dye is detectably altered by enzymatic activity of a viable cell, thereby detecting viable cells in a sample.

Yet additional aspects of the present invention include methods for quantitating viable cells in a sample, comprising providing a sample containing said cells, contacting said cells with molecule or dye that is detectably altered by enzymatic activity of a viable cell, detecting enzymatically altered dye or molecule, thereby detecting the number of viable cells in said sample and obtaining a value therefrom and correlating the detected viable cell value with a standard value, thereby quantitating the viable cells in said sample.

Further aspects include methods for quantitating total and live cells in a sample, comprising measuring total fluorescence of cells in a sample and comparing to a standard value, thereby quantitating total cells in said sample; contacting a sample with a fluorescent dye that is metabolically altered by live cells; said dye having fluorescence properties that are measurably altered when modified by live cells, detecting the metabolic alteration of the dye thereby obtaining a measurement value and comparing said value to a standard value, thereby quantitating live cells in said sample.

Still other aspects of the present invention include methods for measuring the number of total and live yeast, bacteria or other cells in a sample, comprising measuring the native fluorescence of cells in suspension, contacting said cells with a dye that penetrates into the interior of yeast or bacteria and is metabolically modified to a measurable parameter by live cells, measuring the total fluorescence and fluorescence properties provided by the metabolic alteration of said sample and correlating said fluorescence to the number of total and live cells in said sample or a fraction of the sample and determining the percent viability of said sample.

In certain embodiments the cells may be of any origin such as bacteria, yeast, or mammalian. In related embodiments the total cell count is determined by a method selected from the group consisting of native UV absorption, turbidity testing, hemacytometer measurements, fluorescence, and dye exclusion.

In yet other embodiments, the enzymatic activity that alters the dye or molecule is esterase activity. In further embodiments the enzymatically altered dye or molecule is fluorescein diacetate or OREGON GREEN™.

Other embodiments include measurement by a device, such as by a fluorometer.

The invention also provides kits for quantifying yeast or bacteria, comprising a cell suspension solution, a cell penetrating dye, and instructions for detecting dye that correlates to hemacytometer counts, plate counts or other methods of counting viable cells.

In certain embodiments the kit includes a dye that is enzymatically and detectably altered following penetration of viable cells.

In certain aspects a kit for quantifying yeast or bacteria or mammalian cells is provided, comprising: a first container containing a first solution, a second solution containing a compound that penetrates cell membranes and is metabolized to a fluorescent dye or other detectable dye that is measurable, and instructions for using the same.

In other embodiments kits of the invention further comprise a means for mixing said first solution with a sample containing an unknown number of living cells and nonliving cells, means for concentrating the cells from the mixture of said first solution with said sample and removing solids from the remainder of said mixture, and measuring native fluorescence of cells in said solution.

In still yet other embodiments the kits may further comprise a means for mixing said second solution with said cells to form a second mixture, and means for illuminating the mixture of said second solution with said cells with excitation light and measuring fluorescence emitted by said mixture, and thereby determining the amount of metabolically modified dye present in the cells that is proportional to the number of viable cells in said second solution.

In other embodiments the kits may further comprise a third solution containing a compound or compounds that increase the rate of uptake of dye into cells or speed up the rate of conversion of the detectable fluorescent form of the dye inside said cells in second solution.

In another embodiment, a device comprising solid fluorescent material consisting of an adaptor and a compound that can be used to calibrate the instrumentation used for detecting fluorescence in the cells is disclosed.

These and other aspects of the present invention will become evident upon reference to the following detailed description and attached drawings.

BRIEF DESCRIPTION OF THE DRAWINGS

FIG. 2 is a correlation chart of comparable Easy Count readings of total cell counts to total cell counts as determined by methlylene blue.

FIG. 3 is a correlation chart of comparable Easy Count readings of viable cell counts to total cell counts as determined by methlylene blue.

DETAILED DESCRIPTION

Figure 1:
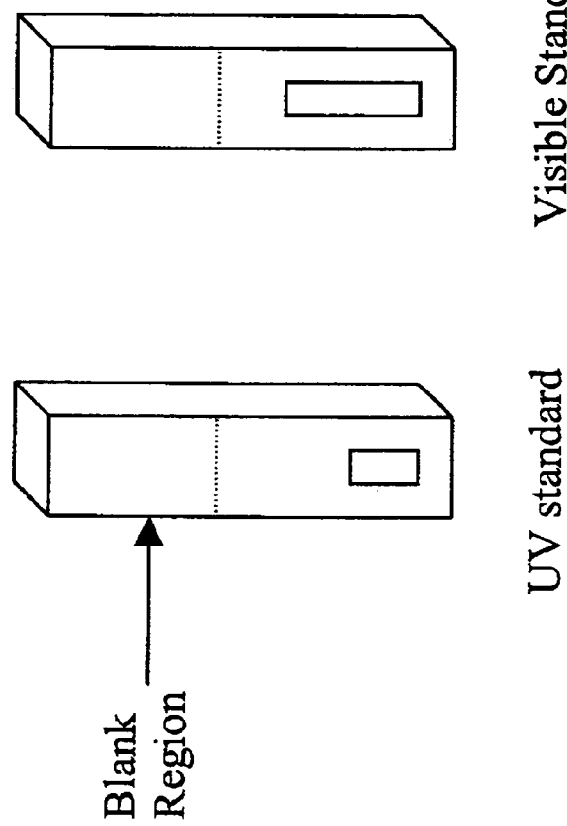
FIG. 1 is an example of solid calibration standards for an ultraviolet and visible wavelength fluorometer.
Figure 4:
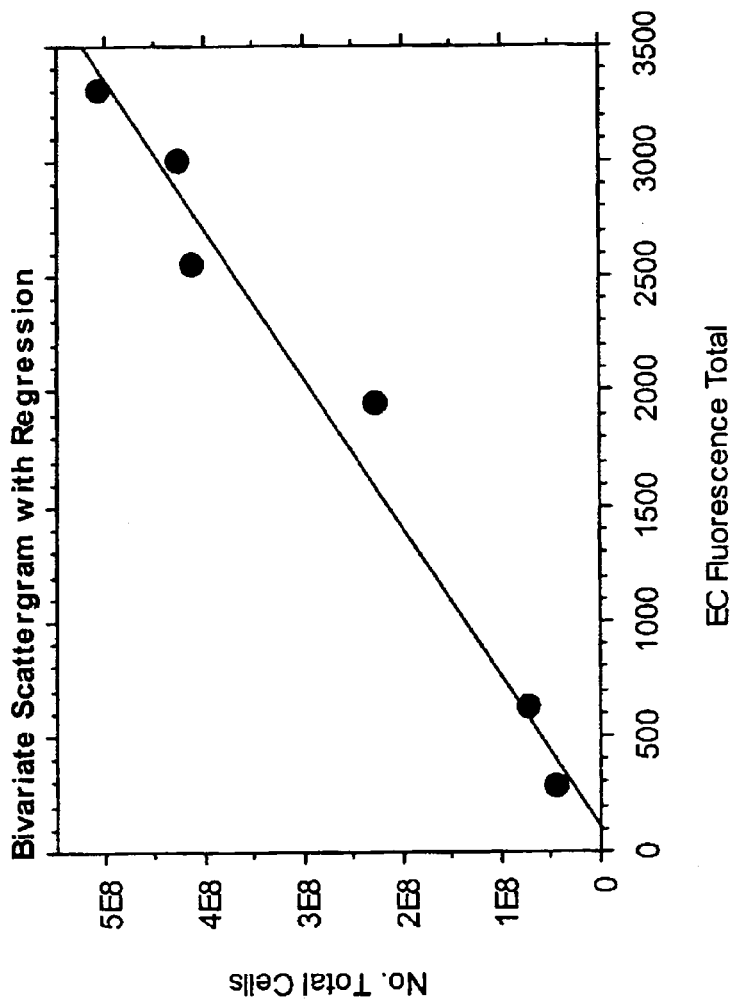
FIG. 4 is a plot of regression analysis demonstrating the relationship between the inventive method and those determined by methylene blue for total cell count.
Figure 5:
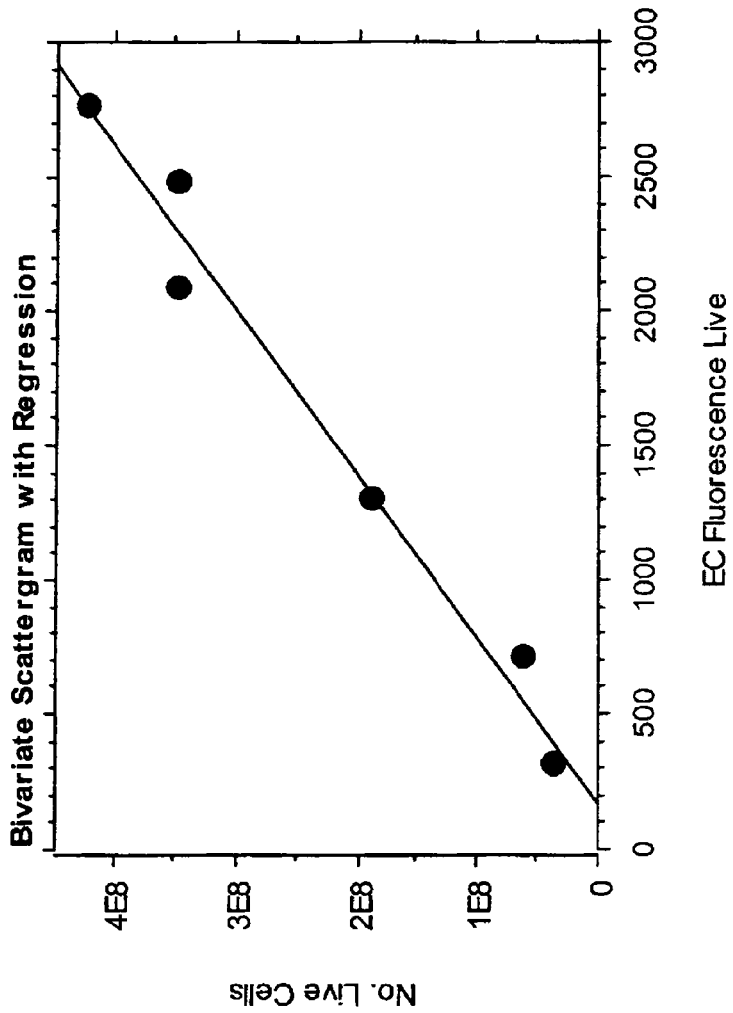
FIG. 5 is a plot of regression analysis demonstrating the relationship between the inventive method and those determined by methylene blue for viable cell counts.

Briefly, the current invention describes novel methods that can be used to quantify live cells and total cells (total includes all cells in the sample, both viable and nonviable) such as yeast and bacteria. This allows the user to determine percent viability of the sample of cells. In one aspect, the instant invention comprises three steps: 1) determination of total cells, 2) determination of viable cells and 3) calculation of percent viability. In certain embodiments the total cells are determined by washing and incubating the cells in a solution and then measuring the native UV fluorescence of the cells in a fluorometer, thereby permitting the determination of total cell populations. Subsequently, the cells are incubated with a compound that can be metabolically converted to a visible fluorescent dye such as fluorescein diacetate, coupled with an inducer of esterase activity such as dequalinium acetate, and then the fluorescence is measured, thus permitting enumeration of viable cell populations. The fluorescent readings are correlated to standard counts such as hemacytometer counts or to the slide viability counts. The two fluorescence readings are directly related to the number of total and viable cells respectively. This permits the user to calculate the percent viability of a mixed population of live and dead cells.

As those of ordinary skill in the art can readily appreciate the present invention may be modified in certain ways to achieve the same result. In brief, the present invention utilizes one or more dyes or molecules that allow for the detection of all cells or total cells (e.g., yeast, bacteria, mammalian, etc.) in a sample and the same or different one or more dyes that are metabolized/derivatized by the viable cells in the sample to allow detection of the viable cells. Accordingly, the percent viability can then be readily determined. As can be appreciated, substances such as detergent-like compounds, surfactants, solvents, or other compounds that affect membrane polarity, membrane fluidity, permeability, potential gradient, etc., may be added to the sample to increase the rate at which the molecule or dye enters the cells in order to speed the process.

Other variations that are within the scope of the present invention include adding compounds that affect membrane polarity to decrease the rate of "leakage" of the converted dye from the cells. Further, esterase enzyme inducing chemicals such as naphthalene or dequalinium acetate may be added to increase esterase activity in living cells. In addition, esterase activity may be increased by environmental factors such as heat. Furthermore, compounds other than fluorescein diacetate, such as Calcein AM, may also be used to detect metabolically active live cells.

The stability and shelf life of the fluorescein diacetate and other chemicals may be increased by the addition of antioxidants or similar preservatives or by dissolving the FDA into other solvents besides acetone or by other stabilizing methods such as lyophilization. The fluorescence detection apparatus used may be designed for microscopic, surface, internal, solution and non-suspension sample formats.

Also included within the context of the present invention is software that permits the user to interface the fluorescence instrumentation to a computer for direct calculation of percent viability and cell concentration or other data processing or recording formats.

Compounds such as hemoglobin may be utilized to reduce background in the sample. Rinsing the sample in a buffer solution and centrifuging or filtering or otherwise retaining the cells as they are washed can be used to remove any exogenous background fluorescence.

The differences between prokaryotes and eukaryotes may also utilized to assist detection. For example, such easily detectable differences include cell membrane receptors, lack of organelles in prokaryotes, or metabolic differences. These differences can be utilized to distinguish between prokaryotes and eukaryotes by using dyes that penetrate only mitochondria or nuclei for example, or to take advantage of membrane and metabolic differences in these two cell types. This will allow the user to count a specific prokaryote or a eukaryote in a mixture of cells that contains both types of cells. For example, one may determine if bacteria contaminate a yeast cell or blood cell population.

Other variations of the present invention include altering the pH of the reaction solutions to increase the sensitivity of the reaction. Further variations include changing concentrations of the solutes to increase or decrease the sensitivity of the reaction. Alterations to the solid standards may be utilized to increase the sensitivity and dynamic range of the assay. The viability assay may be used to measure overall health or metabolic or growth status of the cells, including the ability to withstand stress. The various steps of the tests may be used independently, e.g., to measure only total cells or only live cells.

Other methods of total cell determination may include using DNA binding dyes, protein stains, cell membrane stains, antibody coupled stains, lipid dyes or other methods of detecting total cells in a sample. Viable cells may also be quantified using other methods that distinguish between live and dead cells such as surface markers, DNA stains, protein stains, antibody coupled stains, lipid dyes or other methods of detecting viable cells in a sample.

The solid standard can be made out of other materials such as, but not limited to, plastic, or by embedding chemicals such as fluorescein in a solid matrix of epoxy, acrylic, polyacrylamide or agarose or by coating a material like plastic with said chemical. Other chemicals, which have excitation and emission wavelengths in the range of the dyes or cells used to carry out the invention, could be used.

The instrument can be calibrated with solutions containing fluorescent chemicals such as fluorescein or OREGON GREEN™. Other configurations of the solid standard can be employed. The adaptor can be constructed to fit the type and make of instrument used to carry out the method. Different concentrations of the reagents may be used to carry out the method. Other methods of mixing and or concentrating samples may be used. The wash steps may also be eliminated, thus simplifying the procedure.

Yet further variations of the present invention include, but are not limited to, the use of an incubator to control the temperature of the dye conversion in the cells. Such incubation can take place in a plate counter or vial heater of some kind. Further, the samples may be arranged in an array format to allow high throughput detection.

The methods and kits of the present invention allow for the determination of the number of active cells by measuring the rate of conversion of dye by the cells. The number and activity of said cells may be determined without reaching the reaction endpoint.

The methodology has obvious application in determining the activity of yeast or bacteria in industrial fermentation applications. Thus, the methods and kits can be used to predict the number of cells required to carry out fermentation based on viable cells rather than on total cells.

As those of ordinary skill in the art can readily appreciate, the instant invention can be carried out in a single vessel and solution.

The instant invention also has applicability in assessing the activity, vitality, or number of cells under various storage conditions, comparing the metabolic activity of different cells, developing pitching rate charts for fermentation applications, and use of the method as a self-contained laboratory.

The present invention provides methods, kits and apparatuses for simple dye associated quantitation that allows one to inexpensively determine total cell counts and viable cell counts in a particular sample. An individual of ordinary skill in the art will readily appreciate that alternatives to the steps herein described for quantitating cells may be used and are encompassed herein. Accordingly, all alternatives will use a kit or method wherein a dye is utilized to stain cells and a method is used to detect or quantify the dye. One key aspect of this invention is its ability to simultaneously determine total cells and live cells in a sample in short times compared to standard methods. In preferred embodiments, detection is completed in less than 4 hours, in others in less then about 3 hours, and yet further, in less than about 2 hours, while in specific embodiments, detection is completed in less than about 1 hour, less than about 45 minutes, less than about 30 minutes, less than about 15 minutes, and less than about 10 minutes at low cost.

All patents, patent applications and references cited herein are incorporated in their entirety. Accordingly, incorporated herein by reference are U.S. Pat. Nos. 5,437,980; 5,563,070; 5,582,984; 5,658,751; 5,436,134; 5,939,282; 4,783,401; 3,586,859.

EXAMPLES

Example I

Materials and Calibration

The following shows examples of solutions, volumes and concentrations that can be used to carry out the invention. Other concentrations and volumes and different buffers with different pH values may be used. The samples and reaction solutions may be provided in any volume necessary for detection, however, in the present embodiment, small volumes (less than 1 ml) are utilized such that reagents and sample amounts are kept to a minimum. The volumes and concentrations to be utilized are any that are convenient to the practitioner of the methodology. In certain embodiments, the sample and reagent amounts range from 1 to 10,000 micro liters.

The reader used in the present embodiment is a "picofluor" hand-held fluorometer from Turner Designs, Sunnyvale, Calif. 94086. Any fluorometer that can measure fluorescence at specific wavelengths for detection of the dyes or cells can be employed in the invention. Ideally, the fluorometer can switch back and forth from visible (486 nm excitation with a 10 nm bandwidth and 550 emission with a 10 nm bandwidth) and UV (300-400 nm excitation and 410-700 nm emission) modes without changing filters or making other adjustments; however, this is not necessary to carry out the methodology. Other wavelengths may be used in combination with different dye types or cell types. The wavelength chosen will be dependent on the dye or cell type chosen for staining The instrument needs to be calibrated in a range that permits quantitation of cells. Calibration can be carried out with solutions such as fluorescein or OREGON GREEN™ or with the use of solid standards as described below.

Materials

Solid Calibration Standards:
  Materials
  Colored glass rods: Mint green for the visible mode calibration, and translucent blue for the ultraviolet (UV) mode calibration.
  Solid calibration adapter: Black diacetyl plastic machined to fit the instrument.
  Glass rods are glued into the solid calibration adapter and sealed with a plastic cap,
  (See FIG. 1).

Solutions A (Cell Preparation): 1×PBS
  Ingredients (for 10× stock solution)
  80 grams NaCl
  2.0 grams KCl
  14.4 grams $Na_2HPO_4$
  2.4 grams $KH_2PO_4$
  NaOH (enough to reach a PH of 7.4)
  This recipe makes a 10× stock solution. It must be diluted 1:10 into distilled water to make a 1× working solution before being used.

Solution B (Live Cell Suspension):
 Ingredients: 0.0275 grams dequalinium acetate in
  30 mL 10× Sodium acetate buffer: (13.6 grams Sodium acetate in 100 mL ddH$_2$O)
Stock Solution C (Live Cell Reaction Stock):
 Ingredients:
 Fluorescein diacetate (FDA), 30 mg/10 mL in Acetone
Protocol
 I. Calibration Using Solid Standards
  To calibrate the instrument in "A" mode (UV): Standard Value=500
  1) Remove the mini cell receptacle from the instrument.
  2) Be sure that the instrument is in "A" mode; the letters UV should appear in the lower left corner of the screen.
  3) If the instrument is not in "A" mode, press the A/B key on the instrument keypad.
  4) Press the CAL key on the keypad; when prompted, press ENTER to continue.
  5) When asked to insert the blank, insert the solid standard labeled "A" into the instrument with the letter "A" facing down and to the right.
  6) When asked to insert the "cal", insert the solid standard labeled "A" into the instrument so that the letter A is facing towards you, and the white cap is on top.
  To calibrate the instrument in "B" mode (Visible): Standard Value=500
  1) Follow all the instructions for calibration in "A" mode, making sure that that the instrument is now in "B" mode, and that the solid standard labeled "B" is now being used.

Example II

Total Cell Counts

Total cell counts can be determined by a variety of methodologies, including using the fluorometer noted above. UV operation mode is selected. A fixed volume (200 microliters) of Cell preparation solution is added to the glass sample vial. 5 microliters of sample (yeast cells) is then added to the Cell preparation solution in the vial and centrifuged for about 30 seconds to sediment the cell pellet. The cell pellet is resuspended in about 100 microliters of Cell preparation solution to the sample vial. The sample vial is then read in fluorometer. See FIG. 2.

Example III

Viable Cell Counts

Live cells are quantitated utilizing a dye that is detectably altered by an intracellular enzyme. For example, the fluorometer noted above is set in visible mode and a fixed volume (200 microliters) of Cell preparation solution is added to the sample vial. 5 microliters of sample is added to the solution A in the sample vial and centrifuged for 30 seconds. 100 microliters of Suspension solution is added to the sample vial and 5 microliters of Reaction solution is added to the sample vial. The sample is mixed and placed in the reader and fluorescence determined at time zero and again at 15 minutes. This is the value that will be compared to the Easy Count correlation chart for conversion to cells/ml. See FIG. 3.

Example IV

Yeast Quantitation

Yeast performance is critical to the development of quality beer. For this reason, methods of yeast analysis are an important element of the brewing process. Traditional methods including hemacytometer counting and methylene blue staining are rapid, but inaccurate and unreliable. Slide culture is an accurate measure of yeast viability, but requires a lengthy incubation period of 18 to 24 hours. As an alternative, the fluorometric assay described above is based on the metabolic activity of the yeast culture to provide brewers with a rapid and accurate estimation of active cell number. This method was compared to the hemacytometer counting technique as an estimation of cell number, and to both methylene blue staining and slide culture as measures of vitality and prediction of fermentation performance. The inventive method correlated to the hemacytometer, methylene blue, and slide culture with $R^2$ values of 0.985, 0.987, and 0.962 respectively, $P<0.0001$. An error analysis was carried out by the inventive methods, hemacytometer and methylene blue staining techniques for multiple operators performing the tests. Thus, the present invention could be used to determine correct pitching rates, monitor fermentation and propagation, and for other applications involving cell quantitation.

Yeast

All yeast cultures were obtained from Wyeast Laboratories, Mt. Hood, Oreg. Yeast samples for the experiments comparing the hemacytometer, methylene blue staining, and slide culture to the inventive methods were a 1084 strain of *Saccharomyces cerevisiae*. Yeast cultures tested during laboratory scale fermentations were strain 1968. Brewery scale fermentations were performed using yeast strain 1056.

Hemacytometer Counts

Hemacytometer counts were performed according to the ASBC method (6,8). Samples were removed from a slurry with an initial concentration of 198 million cells per ml, as determined by hemacytometer count, and diluted in spent wort to maintain cell integrity. Each dilution was counted in the hemacytometer as well as measured using the present method. Experiments were carried out in triplicate.

Methylene Blue Staining

Methylene blue staining was performed according to the ASBC method (6,8). Samples were removed from a slurry with an initial concentration of 198 million cells per ml, as determined by hemacytometer count, and diluted in spent wort to maintain cell integrity. Each dilution was stained and counted in a hemacytometer, as well as measured using the present method. Hemacytometer counts were corrected for viability according to the staining results. Experiments were carried out in triplicate.

Slide Culture

Slide culture was performed according to a modified version of the protocol for preparation of slide cultures for the examination of yeast and mold (5). Ten ml of yeast strain 1028 at a concentration of 433 million cells per milliliter, as determined by a hemacytometer count, were placed into a 43° C. water bath. Aliquots were removed at time intervals 0, 2, 4, 6, 8, 10, 15, 20, 30, and 40 minutes. Each was tested using the inventive method. Measurements were taken in triplicate and averaged. Slide culture samples were diluted 1:100 into wort containing 6% gelatin. 10 µl of the sample were then placed on a micro slide, covered and sealed with petroleum jelly. Each slide was incubated for 20 hours at 18° C. before microscopic examination (Microscope model, Leica DMLB). Viability was determined with the assumption that living cells had formed micro colonies, while nonviable cells remained single.

Determination of Active Cell Number Using the Instant Invention

The inventive method for determining total active cell number is based on the metabolic activity of the yeast culture.

The technology involves exposing cells to proprietary chemicals that enter cells through diffusion. These molecules are converted to a fluorescent form by metabolically active cells. This fluorescent signal is quantified in a handheld battery operated fluorometer model GP320 GenPrime Inc, Spokane, Wash. The protocol is as follows: 50 µl of yeast sample was added to 500 µl of cell prep solution in a 1 ml glass test cuvette. 50 µl of dye solution was added; the cuvette was capped, and incubated for 5 minutes. After incubation, the cuvette was shaken, and the fluorescent signal quantitated in the GP320. These values were compared to the hemacytometer and methylene blue staining methods by performing tests with the inventive method on the diluted samples from these experiments. Readings were taken in triplicate and averaged. These relationships were analyzed by linear regression using Statview, SAS institute, Cary N.C.

Fermentation Tracking

Laboratory Scale: Laboratory scale fermentation tracking was carried out in a 300 ml flask by inoculating 150 ml wort with 5 ml yeast strain 1968, with an initial concentration of 420 million cells per ml, and monitoring growth using a hemacytometer and the inventive methods. Cells were grown at room temperature (21° C.). Samples were taken every 45 minutes for 5.25 hours and then periodically over the next 48 hours.

Brewery Scale Brewery Scale fermentation tracking was carried out during a typical fermentation cycle, at the Steam Plant Grill, Spokane, Wash. 99201. Hemacytometer counts and corresponding readings using the instant invention were made daily for 13 days beginning immediately following pitching.

Error

Percent error between operators was determined for the inventive method "Easy Count" method, hemacytometer counts, and the methylene blue staining method. Error analysis was performed using Microsoft Excel.

Hemacytometer: Three operators performed hemacytometer analysis of a yeast strain 1028 slurry according to the ASBC method. Each operator prepared and measured 15 samples. Results were averaged for each operator, and error between operators was calculated.

Methylene Blue: The 15 hemacytometer samples from above were stained with methylene blue according to the ASBC method. Each of the three operators counted stained cells for each sample. Results were averaged for each operator, and error between operators was calculated.

Easy Count: Easy Count tests were performed on 15 replicate samples by each of the three operators. Results were averaged for each operator, and error between operators was calculated.

Hemacytometer Counts

Figure 6:
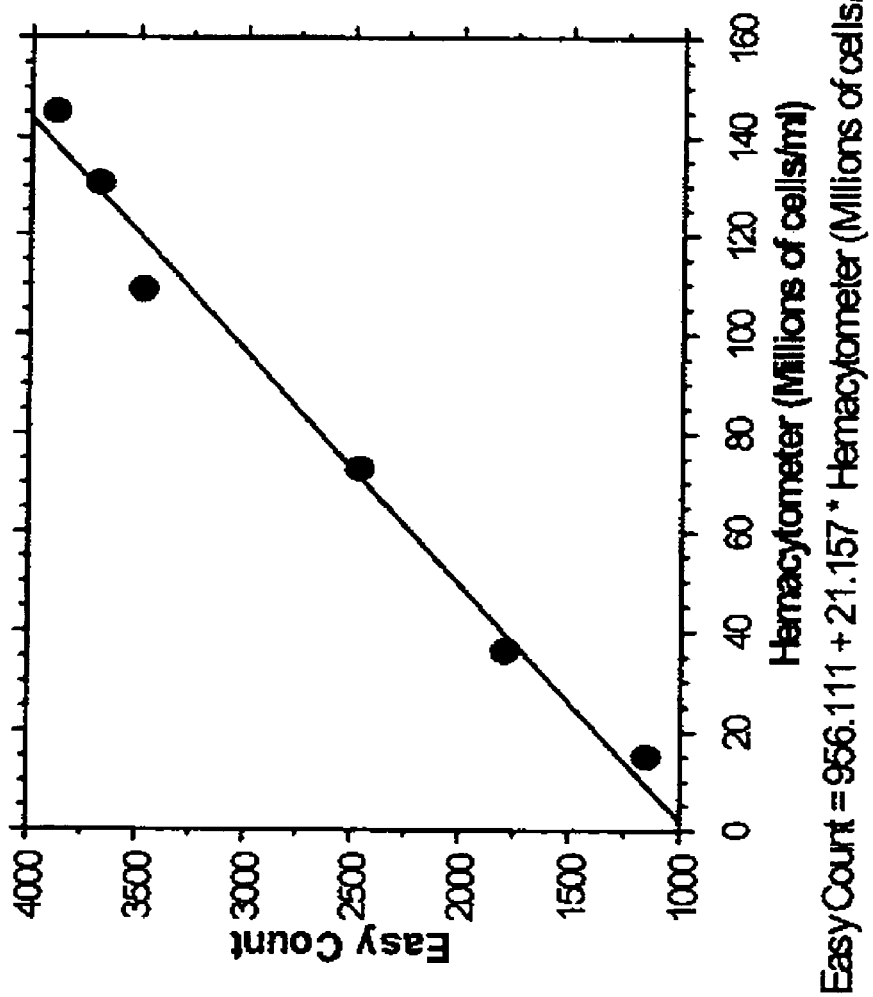
FIG. 6 is a linear correlation plot of hemacytometer counts vs. Easy Count Readings. Data points are the mean of three samples. The linear relationship is significant P<0.0001.

FIG. 6 shows the correlation between the Easy Count values and the cells/ml results of the hemacytometer. A statistically linear relationship was found between cell counts obtained by the ASBC standard method of microscopic examination using a hemacytometer and values obtained using the Easy Count, $R^2=0.985$.

Methylene Blue Staining

Figure 7:
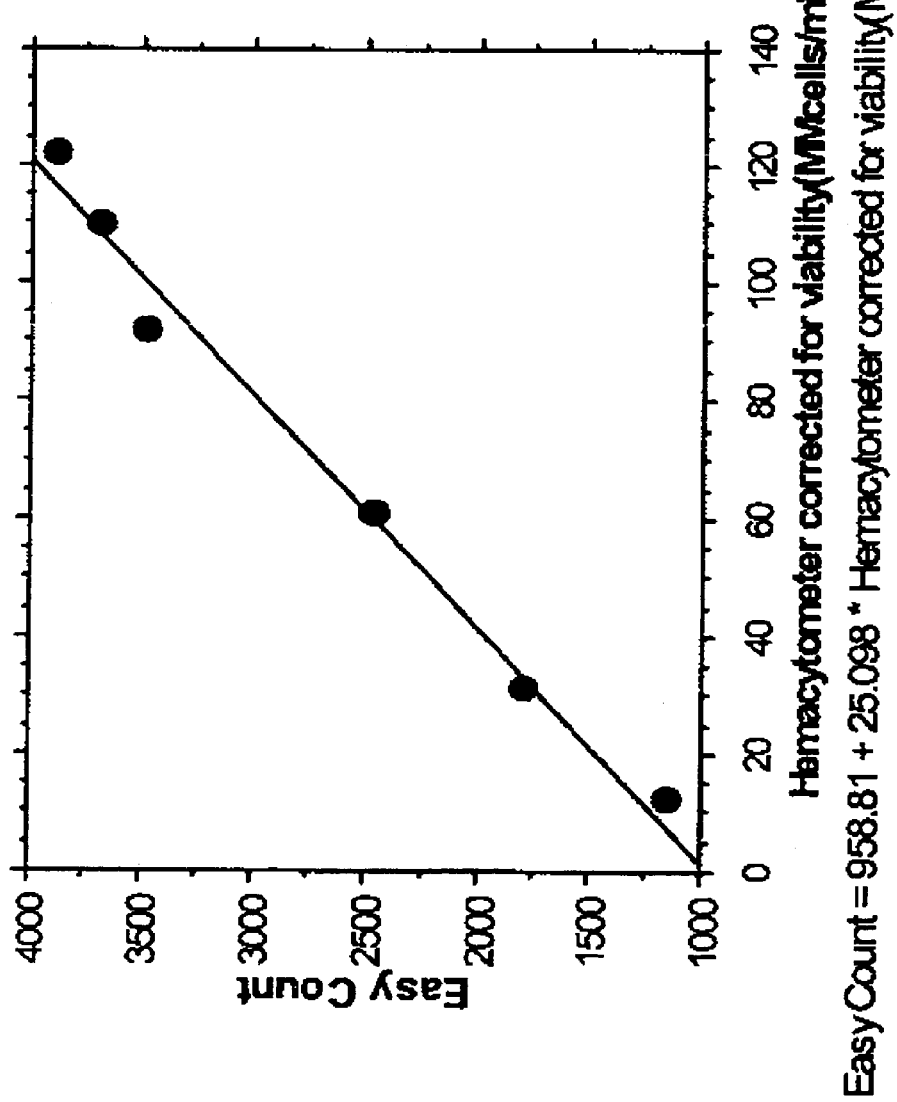
FIG. 7 is a linear correlation plot of hemacytometer counts that have been corrected for viability using methylene blue stain vs. Easy Count Readings. Data points are the mean of three samples. The linear relationship is significant P<0.0001.

FIG. 7 illustrates the linear correlation found between the Easy Count method and the ASBC method for methylene blue staining A statistically linear relationship was found between the Easy Count, and hemacytometer counts corrected for viability, $R^2=0.987$ These results suggest that the Easy Count can be used to accurately predict active cell number. Using the results of the correlation, it is possible for the brewer to accurately determine the correct pitching rate using the Easy Count method based on 1 million active cells per ml per degree plato of wort. Additionally, the method can be used to monitor fermentation, propagation, and for other applications involving the quantitation of cells.

Slide Culture

Figure 8:
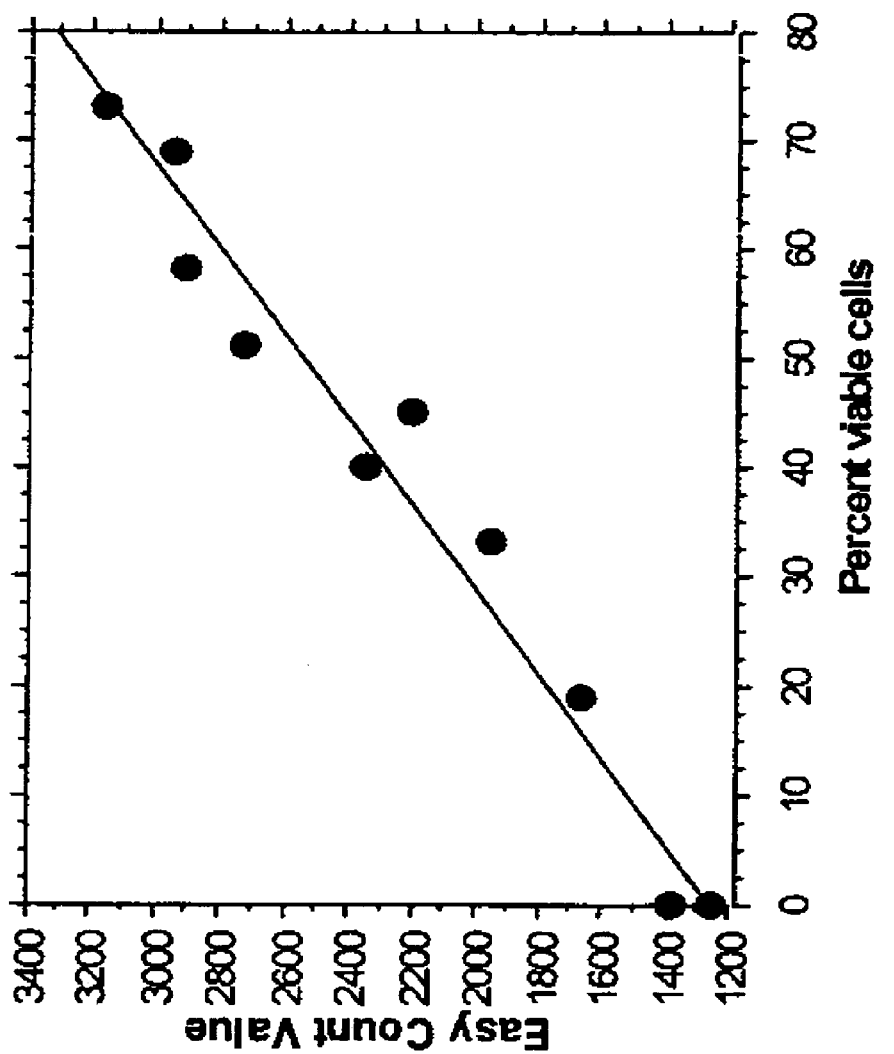
FIG. 8 is a linear correlation between percent viability as measured by slide culture, and Easy Count values. Data points are the mean of three samples. The linear relationship is significant P<0.0001.

A linear relationship was found between the Easy Count and slide culture for yeast viability, as shown in FIG. 8.

The correlation to slide culture confirms that the Easy Count only measures active cells, since the total number of cells in this experiment remains constant.

Fermentation Tracking

Figure 9:
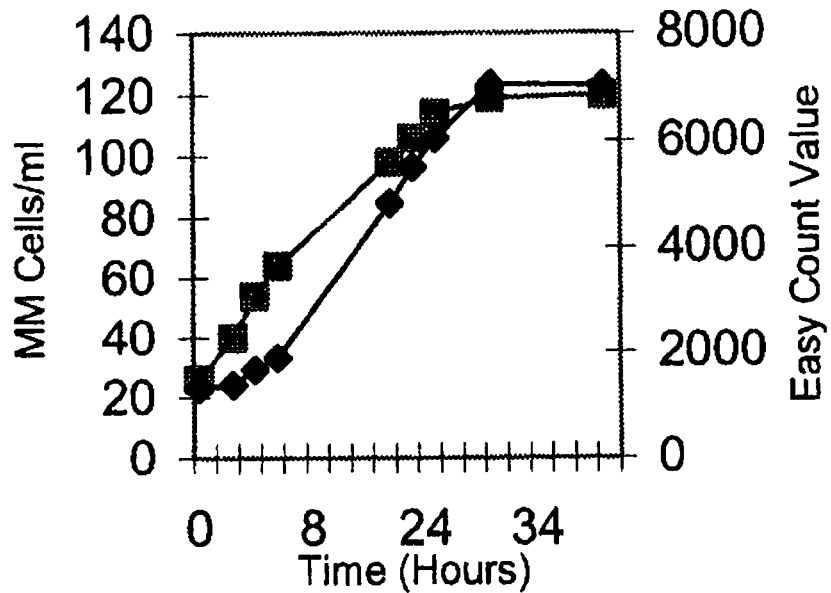
FIG. 9 is a plot representing fermentation tracking Fermentation tracking in a laboratory fermentation using both the Easy Count and hemacytometer methods. Time 0 is the time that the cells were pitched into fresh wort. The Y-axes represent cell counts using a hemacytometer (squares) and active cells using the Easy Count (diamonds). Data points are the mean of three samples.
Figure 10:
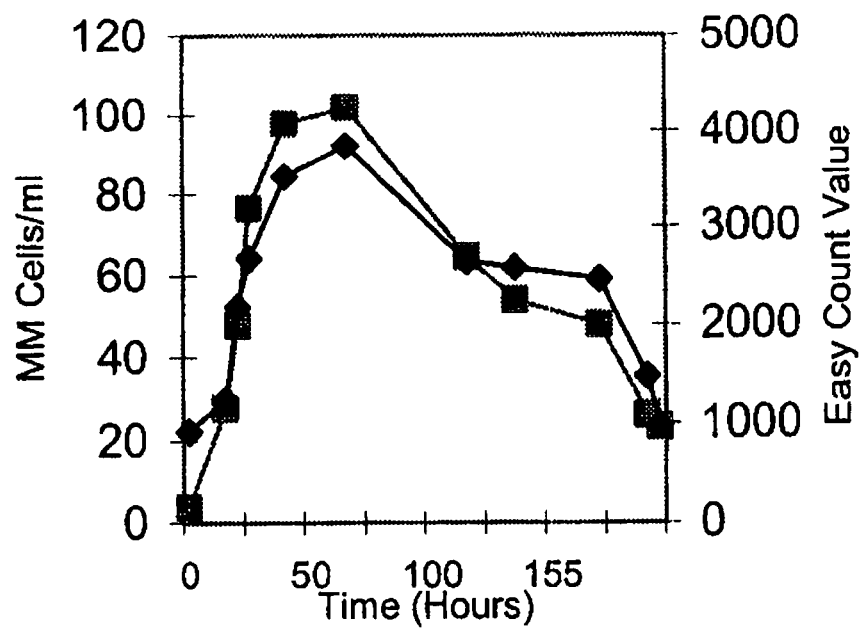
FIG. 10 is a plot representing fermentation tracking during brewery scale fermentation. The Y-axes represent cell counts using a hemacytometer (squares) and the Easy Count (diamonds). Data points are the mean of three samples.

Cell growth was measured during laboratory and brewery scale fermentations using both the ASBC method for hemacytometer counts, and the Easy Count method. FIG. 9 shows cell growth tracked by both methods during laboratory scale fermentation. FIG. 10 is an example of a brewery scale fermentation tracked by both methods.

Error

Figure 11:
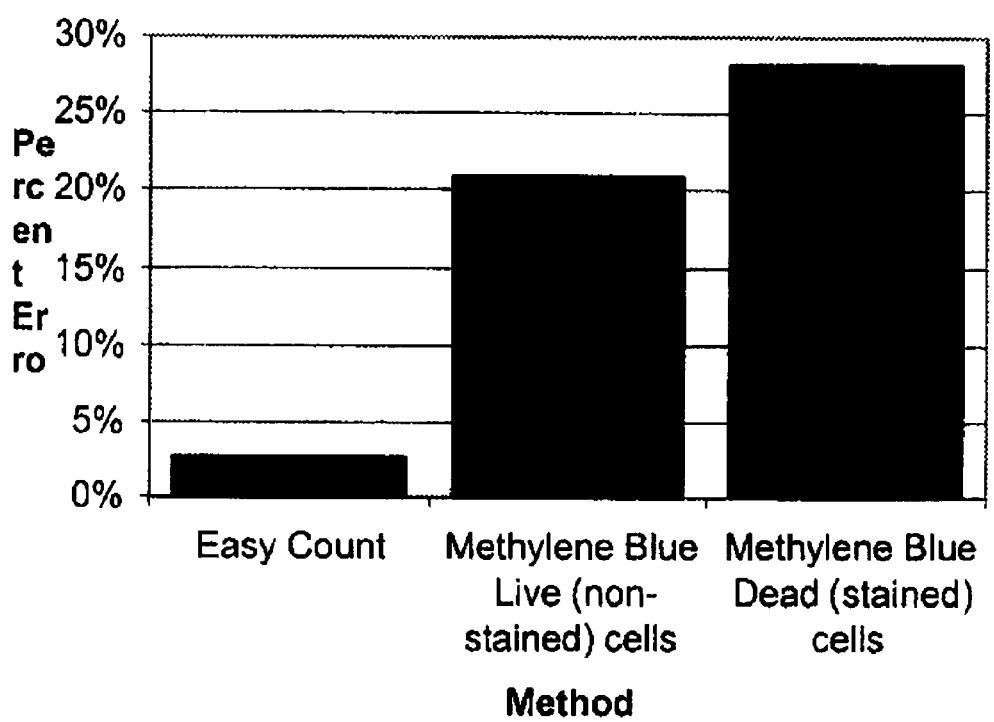
FIG. 11 is a plot depicting Percent error between operators for the three methods shown. Methylene Blue dead (stained) cells reported differences between operators of 28.3%, while Methylene Blue live (non-stained cells) was 21.0%. The error between operators for the Easy Count was significantly lower, at only 2.6%.

Results from the experiments were averaged for each operator as shown in Table 1. Percent error between operators was calculated by dividing the standard deviation of the mean by the mean, and multiplying the result by 100. Easy Count reported significantly lower error between operators than the other methods. These results are graphed in FIG. 11.

TABLE I

| Data in Millions of cells/ml | Easy Count mean | Methylene Blue live mean | Methylene Blue dead mean |
| --- | --- | --- | --- |
| Operator 1 | 195.9 | 158.6 | 27.9 |
| Operator 2 | 197 | 122.3 | 23.6 |
| Operator 3 | 187.7 | 187.7 | 40.3 |
| Mean | 193.5 | 156.2 | 30.6 |
| Std. Dev. | 5.1 | 32.8 | 8.7 |
| % Error | 2.6 | 21.0 | 28.3 |

Results of the error experiments confirm previous research reporting the inaccuracies of hemacytometer counts and methylene blue staining (1, 2, 3, 4, 7). The low error associated with the Easy Count method is an improvement on these traditional techniques.

Percent error is of particular importance to the brewer due to the exacerbation of inaccuracies in the calculation of cells/ml. For example, when calculating cells/ml from a hemacytometer count of 180 live cells and 15 dead cells (counting all 25 fields and using a 1:100 dilution), the result would be 180 million live cells/ml (180*100*10000) and 15 million dead cells/ml (15*100*10000). If the error between operators when performing the live cell test is 21%, then the live cell result could be between 142-218 million cells/ml, a difference of 76 million cells/ml. With a percent error of 28% between operators, the dead cell result could be between 11-19 million cells/ml. This could result in reported viabilities between 87% and 96% for the same sample. The Easy Count has much less error associated with its performance. A reading of 6000 in the Easy Count would be 197 million active cells/ml (see equation generated in FIG. 7.). A percent error of 3% between operators gives a range between 191-203 million cells/ml, a difference of only 12 million cells/ml. The very low error associated with the performance of the Easy Count provides much more reliable information to the brewer.

1. Mochaba, F. et al, Practical Procedures to Measure Yeast Viability and Vitality Prior to Pitching. *J. Am. Soc. Brew. Chem.* 56(1): 1-6, 1998.

2. O'Connor-Cox, E. et al, Methylene Blue Staining: use at your own risk. *Tech. Q. Master. Brew. Assoc.* 34:306-312, 1997
3. Carvell J. P. et at Developments in Using Off-Line Radio Frequency Impedance Methods for Measuring the Viable Cell Concentration in the Brewery. *J. Am. Soc. Brew. Chem.* 58(2): 57-62, 2000
4. Smart, K. A. et al Use of Methylene Violet Staining Procedures to Determine Yeast Viability and Vitality. *J. Am. Soc. Brew. Chem.* 57(1): 18-23, 19992.
5. Harrigan, W. F. Laboratory Methods in Food Microbiology 3$^{rd}$ Ed. Academic Press, San Diego, Calif. 1998
6. American Society of Brewing Chemists. *Methods of Analysis,* 8$^{th}$ Ed. The society, St. Paul. Minn. 1992.
7. Koch, H. A., et al, Fluorescence Microscopy Procedures for Quantitation of Yeasts in Beverages. American Society for Microbiology, 52(3): 599-601, September, 1986.
8. Allen, P. The Microbrewery Laboratory Manual—A Practical Guide to Laboratory Techniques and Quality Control Procedures for Small Scale Brewers, Part 1: Yeast Management. *Brewing Techniques* 2(4): 28-35 July/August, 1994.

Other References:
1. Catt, S. L. Sakkas, D., Bizarro, D. Bianchi, P. G., Maxwell, W. M. and Evans, G.: (1977) Molecular and Human Reproduction 3: 821-825.
2. Ferguson, L. R. and Denny, W. A.: (1995) Mutation Research 329: 19-27.
3. Latt, S. A. and Wohleb, J. D. (1975) Chromosoma 52:297-316.
4. Harrington, W. F., (1998) Laboratory Methods in food Microbiology, Academic Press, San Diego, Calif.
5. Brailsford, M. A. and Gatley, S. (1993) New Techniques in Food and Beverage Microbiology (ed. R. G. Kroll, A Gilmour and M. Sussman), Oxford: Blackwell Scientific.
6. Griffith, C. J. Blucher, A. and Fleri, J. (1994) Food Science and Technology today 8: 209-216
7. Pettipher, G. L. Krollo, R. G. and Fan, L. J. (1989) Rapid Microbiological Methods for Foods, Beverages and Pharmaceuticals (ed C. J. Stannard, S. B. Pettit and F. A. Skinner) Oxford: Blackwell Scientific.
8. Pinder, A. C. Edwards, C., and Clarke, R. G. (1993) New Techniques in Food and Beverage Microbiology (ed. R. G. Kroll, A Gilmour and M. Sussman), Oxford: Blackwell Scientific.
9. Stannard, C. J. Pettit, S. B. and Skinner, F. A. (1989) Rapid Microbiological Methods for Foods, Beverages and Pharmaceuticals (ed C. J. Stannard, S. B. Pettit and F. A. Skinner) Oxford: Blackwell Scientific.
10. Catt, S. L. Sakkas, D., Bizarro, D. Bianchi, P. G., Maxwell, W. M. and Evans, G.: (1977) Molecular and Human Reproduction 3: 821-825.
11. Ferguson, L. R. and Denny, W. A. (1995) Mutation Research 329: 19-27.
12. Atlas, R. M. and Bartha, R. Microbial Ecology, Addison Wesley, Longman, N.Y., (1998).
13. Guldfeldt, L. U. Arneborg, N. Siegumfeldt, H. and Jespersen, L. Relationship between yeast cell proliferation and intracellular esterase activity during brewing fermentations. J. Inst. Brew. 333-338.
14. Breeuwer, P. et al. (1995). Characterization of uptake and hydrolysis of fluorescein diacetate and carboxyfluorescein diacetate by intracellular esterases in *saccharomyces cerevesiae*, which result in accumulation of fluorescent product. Applied and Environmental Microbiology, 61: 1614-1619.
15. Prosperi, E. (1990) Intracellular turnover of fluorescein diacetate. Influence of membrane ionic gradients on fluorescein efflux. Histochemical Journal 22: 227-233.
16. Breeuwer, P. Drocourt, J., Rombouts, F. M. and Abee, T. (1994) Energy-dependent, carrier-mediated extrusion of carboxyfluorescein from *saccharomyces* cerevesiae allows rapid assessment of cell viability by flow cytometry. Applied and Environmental Microbiology, 1467-1472.

The invention claim is:

1. A method for measuring metabolic activity in viable yeast cells, comprising: (a) providing a sample containing yeast cells, (b) contacting said sample containing yeast cells with a molecule or dye that is altered by metabolically active viable yeast cells into a detectably fluorescent form, wherein the molecule or dye is fluorescein diacetate or OREGON GREEN™ (2',7' difluorofluorescein); (c) measuring fluorescence of the molecule or dye that is altered into a detectably fluorescent form by the metabolically active viable yeast cells in said sample; and (d) repeating step (c) over a time course, wherein a change in fluorescence over the time course indicates a change in metabolic activity of viable yeast cells.

2. The method of claim 1, wherein an increase in fluorescence indicates increased metabolic activity in viable yeast cells.

3. The method of claim 1, wherein a decrease in fluorescence indicates decreased metabolic activity in viable yeast cells.

4. The method of claim 1, wherein the yeast is Saccharomyces cerevisiae.

5. The method of claim 1, wherein step (c) further comprises rinsing the sample in a buffer solution and centrifuging or filtering or otherwise retaining the yeast cells as they are washed to remove any exogenous background fluorescence prior to the detection of fluorescence.

6. The method of claim 1, wherein the yeast cells in the sample are concentrated prior to step (b).

7. The method of claim 1, wherein an increase or decrease in fluorescence is used to determine pitching rates.

8. The method of claim 1, wherein an increase or decrease in fluorescence is used to monitor fermentation.

9. The method of claim 1, wherein an increase or decrease in fluorescence is used to monitor yeast propagation.

10. A method for measuring metabolic activity in viable yeast cells, comprising: (a) providing a sample containing yeast cells, (b) contacting said sample containing yeast cells with 1) a molecule or dye that is altered by metabolically active viable yeast cells into a detectably fluorescent form, wherein the molecule or dye comprises fluorescein diacetate or OREGON GREEN™ (2',7' difluorofluorescein), and 2) a compound that increases the rate of uptake of the molecule or dye into the yeast cells or speeds up the rate of conversion of the molecule or dye into a detectably fluorescent form inside said yeast cells; (c) measuring fluorescence of the molecule or dye that is altered into a detectably fluorescent form by the metabolically active viable yeast cells in said sample; and (d) repeating step (c) over a time course, wherein a change in fluorescence over the time course indicates a change in metabolic activity of viable yeast cells.

11. The method of claim 10, wherein an increase in fluorescence indicates increased metabolic activity in viable yeast cells.

12. The method of claim 10, wherein a decrease in fluorescence indicates decreased metabolic activity in viable yeast cells.

13. The method of claim 10, wherein the yeast is Saccharomyces cerevisiae.

14. The method of claim 10, wherein step (c) further comprises rinsing the sample in a buffer solution and centrifuging or filtering or otherwise retaining the yeast cells as they are washed to remove any exogenous background fluorescence prior to the detection of fluorescence.

15. The method of claim 10, wherein the yeast cells in the sample are concentrated prior to step (b).

16. The method of claim 10, wherein an increase or decrease in fluorescence is used to determine pitching rates.

17. The method of claim 10, wherein an increase or decrease in fluorescence is used to monitor fermentation.

18. The method of claim 10, wherein an increase or decrease in fluorescence is used to monitor yeast propagation.

19. A system for measuring metabolic activity in viable yeast, comprising: (a) a molecule or dye that is altered by metabolically active viable yeast cells into a detectably fluorescent form, wherein the molecule or dye comprises fluorescein diacetate or OREGON GREEN™ (2',7' difluorofluorescein); (b) a compound that increases the rate of uptake of the molecule or dye into the yeast cells or speeds up the rate of conversion of the molecule or dye into a detectably fluorescent form inside said yeast cells; and (c) a fluorometer.

* * * * *